US008404825B2

(12) United States Patent
Tittiger et al.

(10) Patent No.: US 8,404,825 B2
(45) Date of Patent: Mar. 26, 2013

(54) METHOD FOR PRODUCING MONOTERPENE AND MONOTERPINOID COMPOUNDS AND USE THEREOF

(75) Inventors: Claus Tittiger, Reno, NV (US); Rubi Figueroa-Teran, Reno, NV (US); Gary J. Blomquist, Sparks, NV (US)

(73) Assignee: Board of Regents of the Nevada System of Higher Education, on Behalf of the University of Nevada, Reno, Reno, NV (US)

( * ) Notice: Subject to any disclaimer, the term of this patent is extended or adjusted under 35 U.S.C. 154(b) by 439 days.

(21) Appl. No.: 12/947,708

(22) Filed: Nov. 17, 2009

(65) Prior Publication Data

US 2012/0107265 A1 May 3, 2012

Related U.S. Application Data

(60) Provisional application No. 61/115,623, filed on Nov. 18, 2008.

(51) Int. Cl.
 *C07H 21/04* (2006.01)
 *C12P 21/06* (2006.01)
 *C12N 5/00* (2006.01)

(52) U.S. Cl. .................. 536/23.2; 435/69.1; 435/252.2; 435/410

(58) Field of Classification Search ........................ None
See application file for complete search history.

*Primary Examiner* — Tekchand Saidha
*Assistant Examiner* — MD. Younus Meah
(74) *Attorney, Agent, or Firm* — Klarquist Sparkman, LLP

(57) ABSTRACT

In various embodiments, the present disclosure provides a method and enzyme for forming various compounds, such as monoterpenes and monoterpenoid compounds. In a specific example, the present disclosure provides a method for producing one or more of (−)-ipsdienol, (−)-ipsenol, ipsenone, and ipsdienone. The present disclosure also provides methods of using compounds formed from the disclosed method and enzyme.

9 Claims, 15 Drawing Sheets

Ipsdienone standard

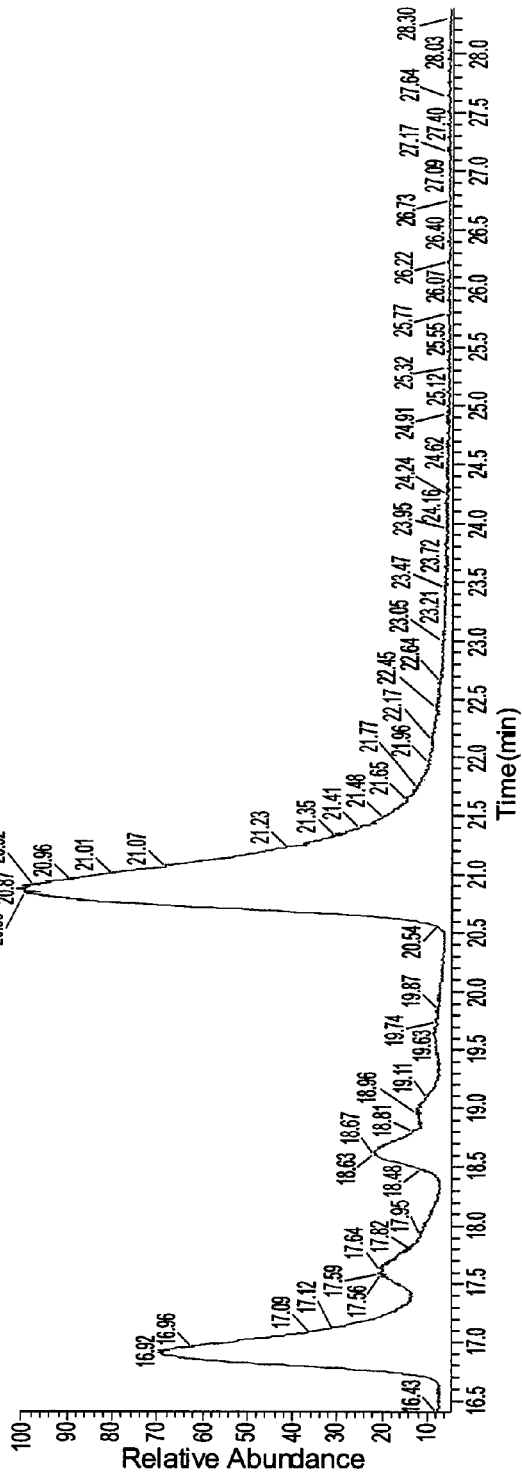
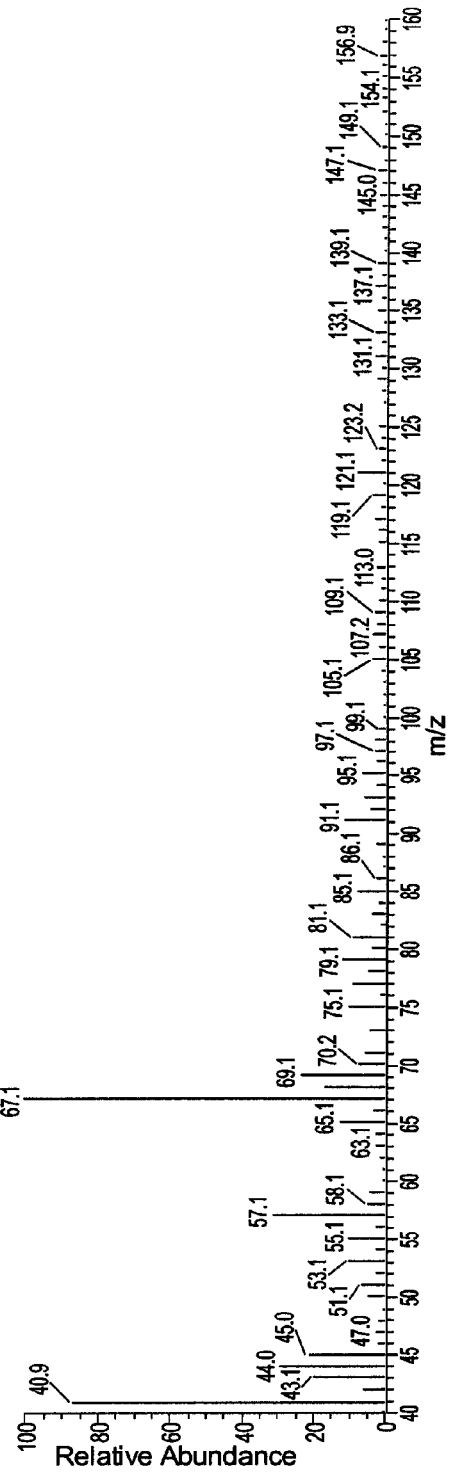
FIG. 18
FIG. 19

SEQUENCE LISTING

```
<160> NUMBER OF SEQ ID NOS: 7

<210> SEQ ID NO 1
<211> LENGTH: 843
<212> TYPE: DNA
<213> ORGANISM: Ips pini

<400> SEQUENCE: 1
ggcgacgaac ttttcaatat ggacactcaa caacctggcg actatacagt tttaaccgat      60
ctcgagtttt ataaaaatca gttgacctaa atgatggtta aaatccagga ttccgtttat     120
ctggtgactg gtggtggatc aggtctgggt gaagccaccg ccaagttatt attgaccgaa     180
ggtgctcgag tgaccatttt cagtcgaaac gaatacaaga atgaatttcc tcatgatcaa     240
gtgttgtccg ttaagggaga tgtgcgttcg gaaagtgatg tgaaaagggc tttagaagct     300
acgatccaga agtttggaaa gttggacggt gtcatgcatt gtgctggcgt ttttcaaaat     360
attgttacta ctaacctcct agggactttt aacgttaaca gactggctat tccgtatttt     420
ttgaccaatc aaccggacga agagggacaa aaagggataa tcatcaattg ctcaagtact     480
tcagggcaca gccctatgtc ttcggcggta gcttacagta ccagcaaagc tgctattata     540
ggtttgagtt atgctttagc caaacaactt agtactctag gtattcgggt aatggatatt     600
gctccagccc tttgtgatac gccaatgttt cgtcgtgcag tcggttttaa tcaggacata     660
gcaaatttcc gtaatttgtt cccagcgaga ctgattcaac ccatcgaata cgcgaacgca     720
gtcaaacata tcatagaaac acccatgttg aatggttcgt cctatcaatt agatggcgct     780
ctcagacctt aaaaatttta taattaataa aaaatatgtg gatgttaaaa aaaaaaaaa     840 aaa                                                                    843

<210> SEQ ID NO 2
<211> LENGTH: 253
<212> TYPE: PRT
<213> ORGANISM: Ips pini

<400> SEQUENCE: 2

Met Met Val Lys Ile Gln Asp Ser Val Tyr Leu Val Thr Gly Gly Gly
1               5                   10                  15

Ser Gly Leu Gly Glu Ala Thr Ala Lys Leu Leu Leu Thr Glu Gly Ala
            20                  25                  30

Arg Val Thr Ile Phe Ser Arg Asn Glu Tyr Lys Asn Glu Phe Pro His
        35                  40                  45

Asp Gln Val Leu Ser Val Lys Gly Asp Val Arg Ser Glu Ser Asp Val
    50                  55                  60

Lys Arg Ala Leu Glu Ala Thr Ile Gln Lys Phe Gly Lys Leu Asp Gly
65                  70                  75                  80

Val Met His Cys Ala Gly Val Phe Gln Asn Gly Asp Glu Leu Phe Asn
                85                  90                  95

Met Asp Thr Gln Gln Pro Gly Asp Tyr Val Leu Thr Asp Ile Val
                100                 105                 110
```

```
Thr Thr Asn Leu Leu Gly Thr Phe Asn Val Asn Arg Leu Ala Ile Pro
        115                 120                 125

Tyr Phe Leu Thr Asn Gln Pro Asp Glu Glu Gly Gln Lys Gly Ile Ile
        130                 135                 140

Ile Asn Cys Ser Ser Thr Ser Gly His Ser Pro Met Ser Ser Ala Val
145                 150                 155                 160

Ala Tyr Ser Thr Ser Lys Ala Ala Ile Ile Gly Leu Ser Tyr Ala Leu
            165                 170                 175

Ala Lys Gln Leu Ser Thr Leu Gly Ile Arg Val Met Asp Ile Ala Pro
        180                 185                 190

Ala Leu Cys Asp Thr Pro Met Phe Arg Arg Ala Val Gly Phe Asn Gln
        195                 200                 205

Asp Ile Ala Asn Phe Arg Asn Leu Phe Pro Ala Arg Leu Ile Gln Pro
        210                 215                 220

Ile Glu Tyr Ala Asn Ala Val Lys His Ile Ile Glu Thr Pro Met Leu
225                 230                 235                 240

Asn Gly Ser Ser Tyr Gln Leu Asp Gly Ala Leu Arg Pro
            245                 250

<210> SEQ ID NO 3
<211> LENGTH: 26
<212> TYPE: DNA
<213> ORGANISM: Artificial sequence
<220> FEATURE:
<223> OTHER INFORMATION: Synthetic oligonucleotide primer.

<400> SEQUENCE: 3
gcgaattcta taaaaatcag ttgacc                                      26

<210> SEQ ID NO 4
<211> LENGTH: 25
<212> TYPE: DNA
<213> ORGANISM: Artificial sequence
<220> FEATURE:
<223> OTHER INFORMATION: Synthetic oligonucleotide primer.

<400> SEQUENCE: 4
gcgaattctt aaggtctgag agcgc                                       25

<210> SEQ ID NO 5
<211> LENGTH: 14
<212> TYPE: PRT
<213> ORGANISM: Artificial sequence
<220> FEATURE:
<223> OTHER INFORMATION: Synthetic peptide.

<400> SEQUENCE: 5

Ser Arg Asn Glu Tyr Lys Asn Glu Phe Pro His Asp Gln Cys
1               5                   10

<210> SEQ ID NO 6
<211> LENGTH: 393
<212> TYPE: DNA
<213> ORGANISM: Artificial sequence
<220> FEATURE:
<223> OTHER INFORMATION: Multiple cloning site for pENTR 4 vector.

<400> SEQUENCE: 6 gggcccccaaa taatgatttt attttgactg atagtgacct gttcgttgca acaaattgat    60
aagcaatgct tttttataat gccaactttg tacaaaaaag caggctccac catgggaacc   120
aattcagtcg actggatccg gtaccgaatt cgcggccgca ttaggcaccc caggctttac   180
```

```
actttatgct tccggctcgt aaggtcgacg aattcgcggc cgcactcgag atatctagac      240
ccagctttct tgtacaaagt tggcattata agaaagcatt gcttatcaat ttgttgcaac      300
gaacaggtca ctatcagtca aaataaaatc attatttgcc atccagctgc agctctggcc      360
cgtgtctcaa aatctctgat gttacattgc aca                                  393

<210> SEQ ID NO 7
<211> LENGTH: 378
<212> TYPE: DNA
<213> ORGANISM: Artificial sequence
<220> FEATURE:
<223> OTHER INFORMATION: Multiple cloning site for pENTR 4 vector.

<400> SEQUENCE: 7
cccggggttt attactaaaa taaaactgac tatcactgga caagcaacgt tgtttaacta       60
ttcgttacga aaaatatatta cggttgaaac atgtttttc gtccgagttg gtacccttgg     120
ttaagtcagc tgacctaggc catggcttaa gcgccggcgt aatccgtggg gtccgaaatg     180
tgaaatacga aggccgagca ttccagctgc ttaagcgccg gcgtgagctc tatagatctg     240
ggtcgaaaga acatgtttca accgtaatat tctttcgtaa cgaatagtta aacaacgttg     300
cttgtccagt gatagtcagt tttatttttag taatttttagt aatcagctca gagttttaga   360
gactacaatg taacgtgt                                                   378
```

METHOD FOR PRODUCING MONOTERPENE AND MONOTERPINOID COMPOUNDS AND USE THEREOF

CROSS REFERENCE TO RELATED APPLICATION

This application claims the benefit of, and incorporates by reference, U.S. Provisional Patent Application No. 61/115,623, filed Nov. 18, 2008.

STATEMENT OF GOVERNMENT SUPPORT

The invention was made by an agency of the United States Government or under a contract with an agency of the United States Government. The name of the U.S. Government agency and the Government contract number are: National Science Foundation; Grant/Contract Nos. 0719279 and 0642182. The U.S. Government has certain rights in the invention.

FIELD

The present disclosure generally relates to a method for synthesizing monoterpenes and monoterpenoid compounds and a method for the use of such compounds. In a specific example, the present disclosure provides a method for producing one or more of (−)-ipsdienol, (−)-ipsenol, ipsenone, and ipsdienone.

BACKGROUND

Monoterpenes and related compounds (monoterpenoid alcohols, ketones, etc.) are a structurally diverse group of chemicals that share a common two-isoprene (2-methylbuta-1,3-diene) basic structure. They have broad uses industrially as solvents (e.g. turpentine) or as flavorants or scents. They are produced naturally mostly by plants: in the rinds of citrus fruits, or leaves of some species, or in the woody tissue of coniferous trees. For example, pine tree resin contains high monoterpene levels and is a major source of turpentine.

Some monoterpenes and monoterpenoids are chiral, that is, they have a "handedness." Molecules that are structural "mirror images" of each other are called enantiomers. Enantiomers are usually referred to as "(+)" and "(−)"; "R" and "S", or "D" and "L". Although different enantiomers are chemically identical, their biochemical or physiological properties can be very different. For example, (+)-limonene has a citrus smell, while (−)-limonene smells like turpentine. A mixture of equal amounts of both enantiomers of a chiral compound is called a racemic mixture.

Pine bark beetles are closely linked to monoterpenes because they live in the phloem of pine trees, where they are exposed to and must deal with high monoterpene concentrations. Also, most species rely on monoterpenoid-based pheromonal communication to successfully attack a host tree. The enantiomeric composition of the pheromone blend is important. For example, the aggregation pheromone of western populations of *Ips pini* consists of ~95% (−)-ipsdienol(2-methyl-6-methylene-2,7-octadien-4-ol) while a racemic mixture is not attractive at all. In contrast, populations of *I. pini* from eastern North America use racemic ipsdienol as a pheromone. A related species endemic to the southeast U.S., *I. calligraphus*, is attracted to (−)-ipsdienol, but dispersed by (+)-ipsdienol.

There are a number of commercially important pine bark beetle species. For example, *Ips calligraphus* is distributed across mostly eastern North America. As mentioned above, *I. calligraphus* responds to (R)-(−)-ipsdienol. Like other scolytids, *Ips* spp. periodically cause loss of wood (cut wood and sometimes standing trees) over extensive areas. Their galleries do not affect the structural properties of the wood significantly, but may render it useless for veneer or furniture making. However, they tend to be less aggressive and less host-specific than *Dendroctonus* spp. They mostly breed in slash, or in broken, fallen or dying trees, but *I. calligraphus* can, under favorable, conditions make successful primary attacks on healthy *Pinus* stands.

*I. calligraphus* forms part of the so-called "southern pine bark beetle guild" (including also *Dendroctonus frontalis, D. terebrans, I. grandicollis* and *I. avulsus*), which attacks disturbed *Pinus* spp. in southeastern USA (e.g. disturbance by lightning strike, attacks by defoliating insects) and also causes economic problems by infesting freshly cut logs and pulpwood and introducing bluestain fungi. Published information on *I. calligraphus* as a pest relates almost exclusively to this area and to the Caribbean. It is considered only a secondary pest in California. Subsp. *ponderosae*, though reportedly widespread in western USA, is not considered as a pest there.

*Ips confusus* is distributed across the western US. *I. confusus* infests pinyon pine trees and causes periodic, severe, widespread damage. This species responds to (+)-ipsdienol and ipsenol. They mostly breed in slash, or in broken, fallen or dying trees. In this way, *I. confusus* can kill pinyon pines in southwest USA, when outbreaks start on trees that are damaged or uprooted in land-clearance schemes. *I. paraconfusus* is of greater practical importance because it attacks the timber tree *P. ponderosa*, killing saplings and young trees up to about 65 cm in diameter. Outbreaks develop on recently cut wood and spread to nearby living trees. This is reflected by a much greater number of publications on *I. paraconfusus* than on *I. confusus*. Top-killing by *I. paraconfusus* can contribute to outbreaks of the more dangerous pest *Dendroctonus brevicomis*.

*Ips. typographus* is distributed across northern Europe and Asia. This species responds to ipsenol as an anti-aggregation pheromone. *I. typographus* is the most destructive species of the genus *Ips*, and probably the most serious pest on spruce in Europe. There are records of outbreaks dating from the eighteenth century. Those outbreaks resulted in the loss of million of cubic meters of wood.

SUMMARY

Representative embodiments of the present disclosure are described in the appended claims. There are additional features and advantages of the various embodiments of the present disclosure. They will become evident from the following disclosure.

In this regard, it is to be understood that the appended claims are a brief summary of the various embodiments described herein. Any given embodiment of the present disclosure need not provide all features noted above, nor must it solve all problems or address all issues in the prior art noted above.

BRIEF DESCRIPTION OF THE DRAWINGS

FIG. 18 is a gas chromatogram of the reaction product produced by the action of Ipi12D04 enzyme on ipsenone.

FIG. 19 is a mass spectrum of the reaction product produced by the action of Ipi12D04 enzyme on ipsenone.

DETAILED DESCRIPTION

Figure 1:
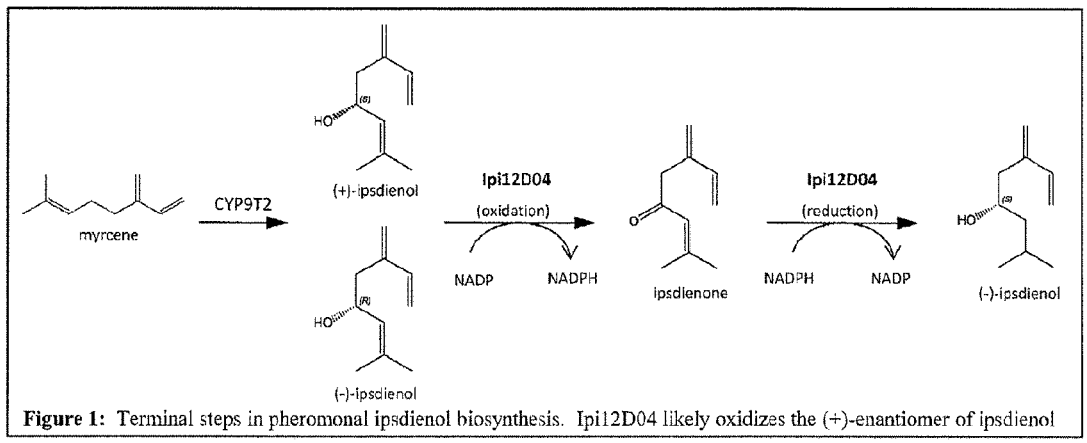
FIG. 1 is schematic diagram illustrating terminal steps in pheromonal ipsdienol biosynthesis.
Figure 2:
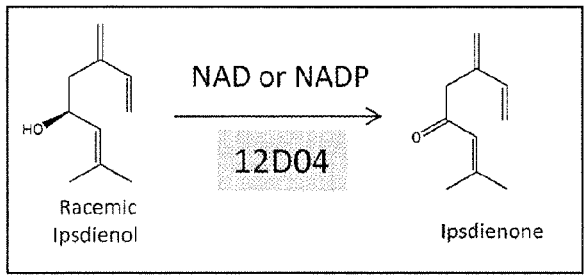
FIG. 2 is a schematic diagram illustrating the use of Ipi12D04 to convert racemic ipsdienol to ipsdienone in the presence of NAD or NADP.
Figure 3:
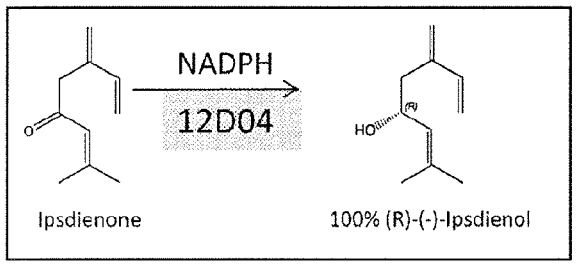
FIG. 3 is a schematic diagram illustrating the use of Ipi12D04 to convert ipsdienone to optically pure (−)-ipsdienol in the presence of NADPH.
Figure 4:
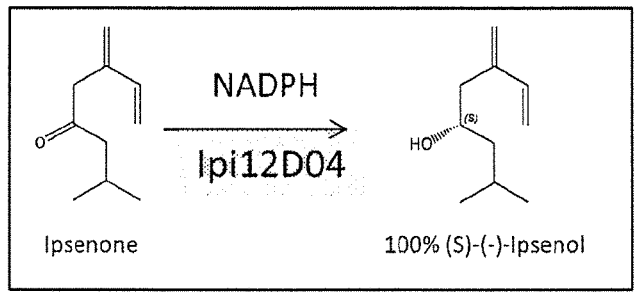
FIG. 4 is a schematic diagram illustrating the use of Ipi12D04 to convert ipsenone to optically pure (−)-ipsenol in the presence of NADPH.

Unless otherwise explained, all technical and scientific terms used herein have the same meaning as commonly understood by one of ordinary skill in the art to which this disclosure belongs. In case of conflict, the present specification, including explanations of terms, will control. The singular terms "a," "an," and "the" include plural referents unless context clearly indicates otherwise. Similarly, the word "or" is intended to include "and" unless the context clearly indicates otherwise. The term "comprising" means "including;" hence, "comprising A or B" means including A or B, as well as A and B together. All numerical ranges given herein include all values, including end points (unless specifically excluded) and any and all intermediate ranges between the endpoints.

Although methods and materials similar or equivalent to those described herein can be used in the practice or testing of the present disclosure, suitable methods and materials are described herein. The disclosed materials, methods, and examples are illustrative only and not intended to be limiting.

In one aspect, the present disclosure provides a polynucleotide, such as a cDNA or a RNA, and its encoded enzyme, collectively referred to herein as "Ipi12D04." Ipi12D04 is also intended to embrace modified polynucleotides and polynucleotide fragments based on, similar to, or related to, Ipi12D04 that encode enzymes which exhibit oxidase or reductase activity, such as those capable of acting on at least some of the substrates as native Ipi12D04 enzyme. Ipi12D04 is also intended to embrace the enzymes produced by such modified polynucleotides or polynucleotide fragments. The Ipi12D04 enzyme can be used in various forms, including crude cell extracts, isolated enzyme, or purified enzyme. In some cases, the Ipi12D04 enzyme is produced by a transgenic host cell into which an Ipi12D04 polynucleotide has been introduced. In other cases, the Ipi12D04 enzyme is synthetically produced. The Ipi12D04 enzyme, in another implementation, is isolated, such as from an organism.

In a specific embodiment, a cDNA of the present disclosure was identified from an expressed sequence tag clone generated from *Ips pini* cDNA library plate #012, clone D04. The associated gene is encoded in the genome of the pine engraver, *Ips pini*, a bark beetle that has a host range across most of North America. The cDNA sequence was determined to be the sequence shown below in SEQ ID NO:1:

```
  1                                      M   M   V   K   I   Q   D   S   V   Y
  1 CTCGAGTTTTATAAAAATCAGTTGACCTAAATGATGGTTAAAATCCAGGATTCCGTTTAT

21 L   V   T   G   G   G   S   G   L   G   E   A   T   A   K   L   L   L   T   E
 61 CTGGTGACTGGTGGTGGATCAGGTCTGGGTGAAGCCACCGCCAAGTTATTATTGACCGAA

41 G   A   R   V   T   I   F   S   R   N   E   Y   K   N   E   F   P   H   D   Q
121 GGTGCTCGAGTGACCATTTTCAGTCGAAACGAATACAAGAATGAATTTCCTCATGATCAA

61 V   L   S   V   K   G   D   V   R   S   E   S   D   V   K   R   A   L   E   A
181 GTGTTGTCCGTTAAGGGAGATGTGCGTTCGGAAAGTGATGTGAAAAGGGCTTTAGAAGCT

81 T   I   Q   K   F   G   K   L   D   G   V   M   H   C   A   G   V   F   Q   N
241 ACGATCCAGAAGTTTGGAAAGTTGGACGGTGTCATGCATTGTGCTGGCGTTTTTCAAAAT

101 G   D   E   L   F   N   M   D   T   Q   Q   P   G   D   Y   T   V   L   T   D
301 GGCGACGAACTTTTCAATATGGACACTCAACAACCTGGCGACTATACAGTTTTAACCGAT

121 I   V   T   T   N   L   L   G   T   F   N   V   N   R   L   A   I   P   Y   F
361 ATTGTTACTACTAACCTCCTAGGGACTTTTAACGTTAACAGACTGGCTATTCCGTATTTT
```

```
                                -continued
141  L   T   N   Q   P   D   E   E   G   Q   K   G   I   I   I   N   C   S   S   T
421  TTGACCAATCAACCGGACGAAGAGGGACAAAAAGGGATAATCATCAATTGCTCAAGTACT 161  S   G   H   S   P   M   S   S   A   V   A   Y   S   T   S   K   A   A   I   I
481  TCAGGGCACAGCCCTATGTCTTCGGCGGTAGCTTACAGTACCAGCAAAGCTGCTATTATA 181  G   L   S   Y   A   L   A   K   Q   L   S   T   L   G   I   R   V   M   D   I
541  GGTTTGAGTTATGCTTTAGCCAAACAACTTAGTACTCTAGGTATTCGGGTAATGGATATT 201  A   P   A   L   C   D   T   P   M   F   R   R   A   V   G   F   N   Q   D   I
601  GCTCCAGCCCTTTGTGATACGCCAATGTTTCGTCGTGCAGTCGGTTTTAATCAGGACATA 221  A   N   F   R   N   L   F   P   A   R   L   I   Q   P   I   E   Y   A   N   A
661  GCAAATTTCCGTAATTTGTTCCCAGCGAGACTGATTCAACCCATCGAATACGCGAACGCA 241  V   K   H   I   I   E   T   P   M   L   N   G   S   S   Y   Q   L   D   G   A
721  GTCAAACATATCATAGAAACACCCATGTTGAATGGTTCGTCCTATCAATTAGATGGCGCT 261  L   R   P   -
781  CTCAGACCTTAAAAATTTTATAATTAATAAAAAATATGTGGATGTTAAAAAAAAAAAAA 281
841  AAA
```

The full-length cDNA is 843 nucleotides long and includes a 762 nucleotide open reading frame.

The Ipi12D04 enzyme encoded by the Ipi12D04 cDNA appears to be to natively "tune" the enantiomeric composition of male-produced ipsdienol: Myrcene is first converted to ~80%:20% (−)-:(+)-ipsdienol by a cytochrome P450 (CYP9T2). Ipi12D04 then apparently acts on the (+)-enantiomer, first oxidizing it to ipsdienone, and then reducing the ketone stereo-specifically to (−)-ipsdienol. A schematic diagram of this process is illustrated in FIG. 1.

The present disclosure thus provides a method of producing the Ipi12D04 enzyme. In one example, the method includes producing transgenic cells, such as insect cells, with the Ipi12D04 cDNA. The transformed cells express the Ipi12D04 enzyme, which can then be isolated and purified.

Ipi12D04 enzyme can be used to stereospecifically interconvert various monoterpines and monoterpinoids, including ipsdienol, ipsenol, ipsdienone, and ipsenone. For example, Ipi12D04 enzyme can be used to convert ipsenone stereospecifically to (−)-ipsenol. Ipi12D04 enzyme can also be used to convert ipsdienone stereospecifically to (−)-ipsdienol. Ipi12D04 enzyme can be used to convert ipsensol or ipsdienol to the corresponding ketone. The ketones, as explained above, can then be sterospecifically converted to (−)-alcohol using Ipi12D04 enzyme.

In some examples of the method of the present disclosure, a compound produced by the action of Ipi12D04, including one or more of (−)-ipsdienol, (−)-ipsenol, ipsdienone, or ipsenone produced using Ipi12D04 is used in an insect control composition. These substances may be mixed with other compounds, including attractants, dispersants, or insecticides. For example, the substances may be mixed with other semiochemicals to tune a composition to a desired function, such as attracting or dispersing a particular insect species. In a more particular example, (−)-ipsdienol is mixed with one or more of (+)-ipsdienol, (−)-ipsenol, (+)-ipsenol, ipsdienone, or ipsenone. In another example, (−)-ipsenol is mixed with one or more of (+)-ipsenol, (−)-ipsdienol, (+)-ipsdienol, ipsdienone, or ipsenone. According to a more particular method, a pheromone blend of a particular insect species, such as a bark beetle species, is created using one or more of (−)-ipsdienol, (−)-ipsenol, ipsenone, or ipsdienone produced using Ipi12D04. Suitable insecticides include, without limitation, pyrethrin or pyrethroid toxins, which may be natural or synthetic, esfenvalerate, malathion, dimethoate, bifenthrin, and O,O-dimethyl O-(2,4,5-trichlorophenyl)-phosphorothioate; zetacypermethrin, and mixtures thereof.

The disclosed compositions may include additional ingredients, including those used to promote dispersion, stability, or efficacy. For example, ingredients can be used to control the release rate of the active agent or agents.

The present disclosure also provides devices for dispersing a composition according to the present disclosure or devices to which a composition of the present disclosure has been applied. For example, a composition of the present disclosure may be manufactured in a spray bottle or spray can. When the composition is used as a dispersant, the composition may be dispensed on or proximate items to be protected, such as trees or fallen logs. When used as an attractant, the composition is, in one example, placed at location sufficiently remote from items to be protected, such as timber stands, fallen logs, or lumber piles. Alternatively or additionally, the composition may be mixed with, or placed proximate to, insecticidal compositions or used to lure insects into a physical trap. Attractant compositions may also be used in order to assist in monitoring insect populations.

The composition may be placed in a suitable trap or other device. For example, the composition may be placed in a suitable device, such as a bubble gap, having a permeable barrier through which the composition may be released. The composition may also be impregnated into various materials, including polymers, hydrogels, microbeads, clays, rubber, or cellulose.

The proper semiochemical mixture needed to attract or disperse a particular species, as well as the amount of a particular composition to be used for a particular application, is within the skill of the ordinary art worker to determine, including using empirical methods.

In another aspect, the present disclosure provides transgenic cells into which an Ipi12D04 polynucleotide has been inserted. The present disclosure also provides for enzymes expressed by such transgenic cells. In yet another aspect, the present disclosure provides compounds produced by the action of such enzymes on a substrate. Additional aspects of the present disclosure are described in the appended claims.

EXAMPLE

Figure 5:
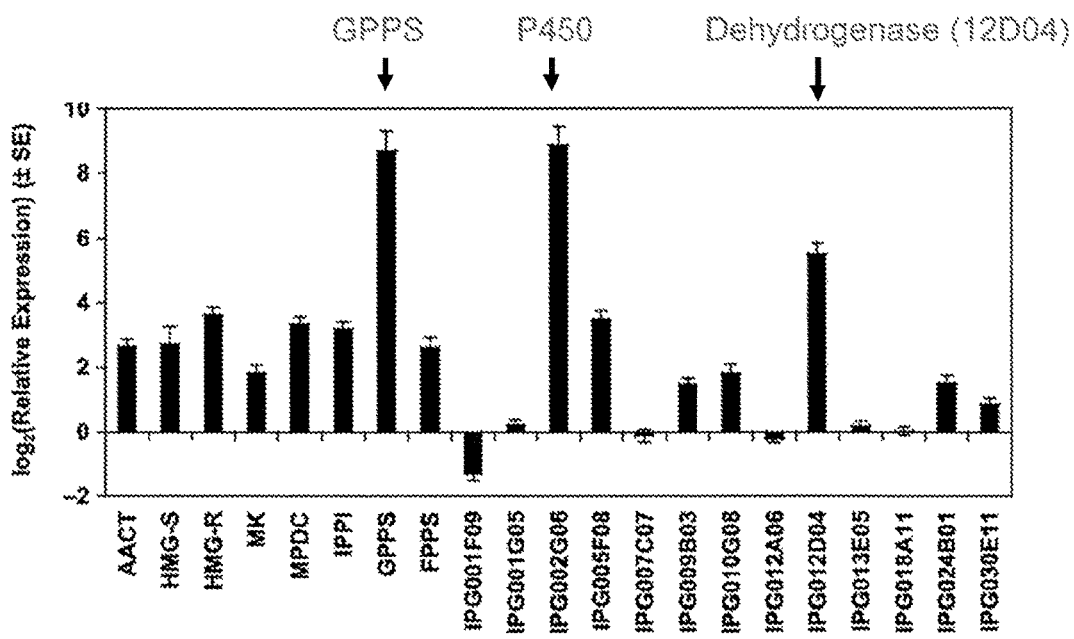
FIG. 5 is a graph of qRT-PCR data (log of relative expression in males versus females for various mRNA) illustrating relative basal mRNA expression levels between male and female pine beetles treated with JH III.
Figure 6A:
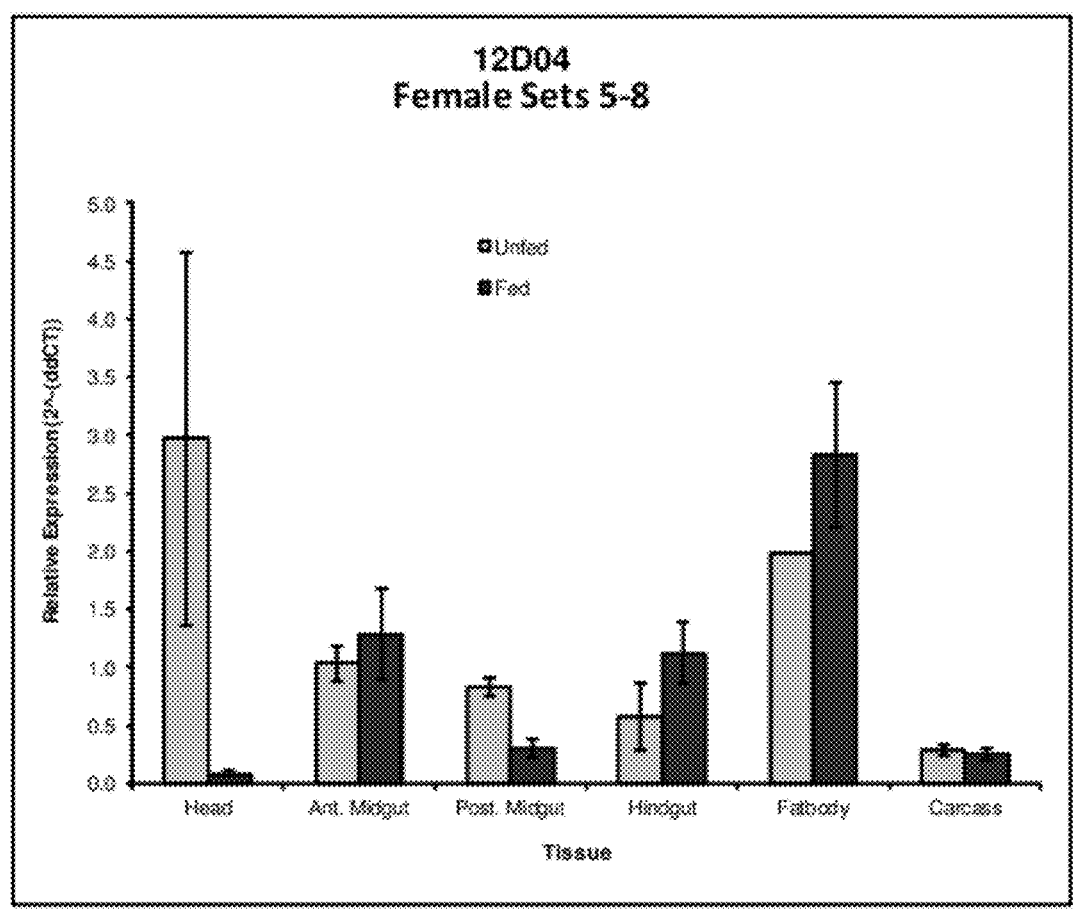
FIG. 6 is graphs of qRT-PCR data illustrating differences in Ipi12D04 mRNA levels in various tissues of male (right graph) and female (left graph) *I. pini* beetles.
Figure 6B:
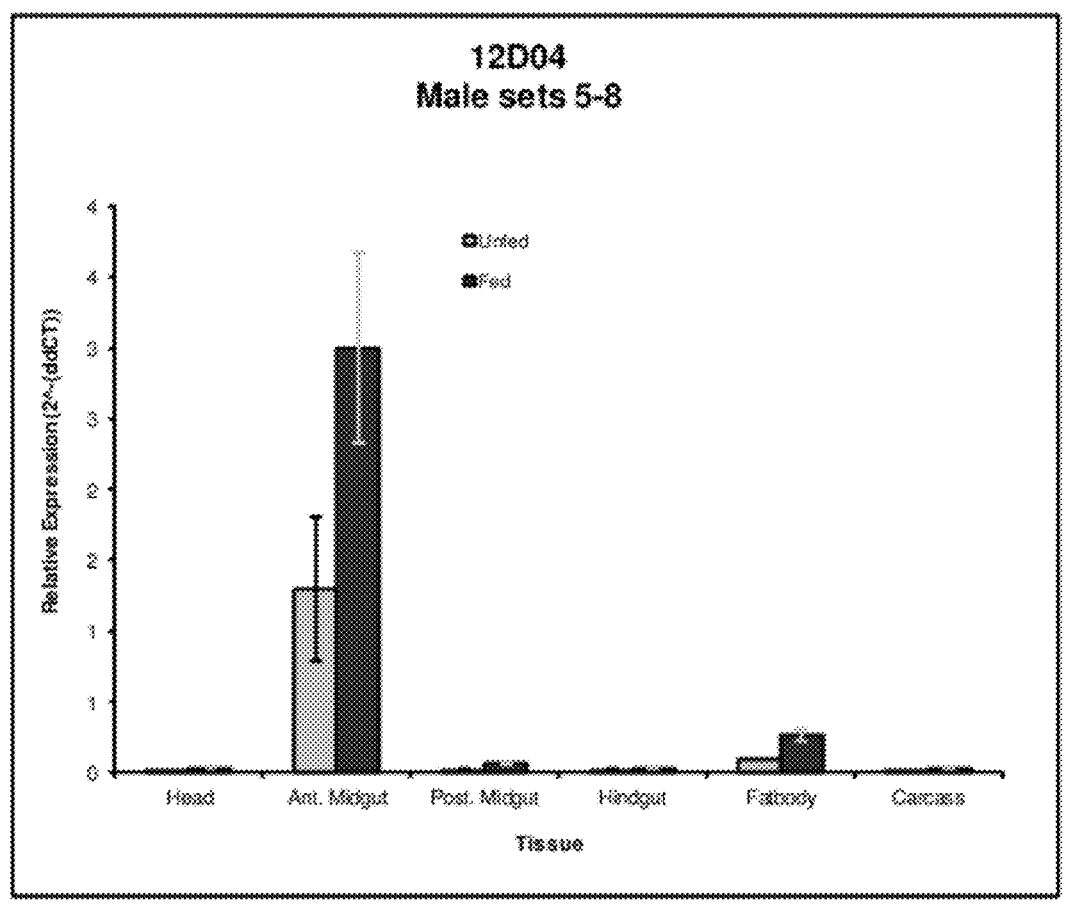
Figure 7A:
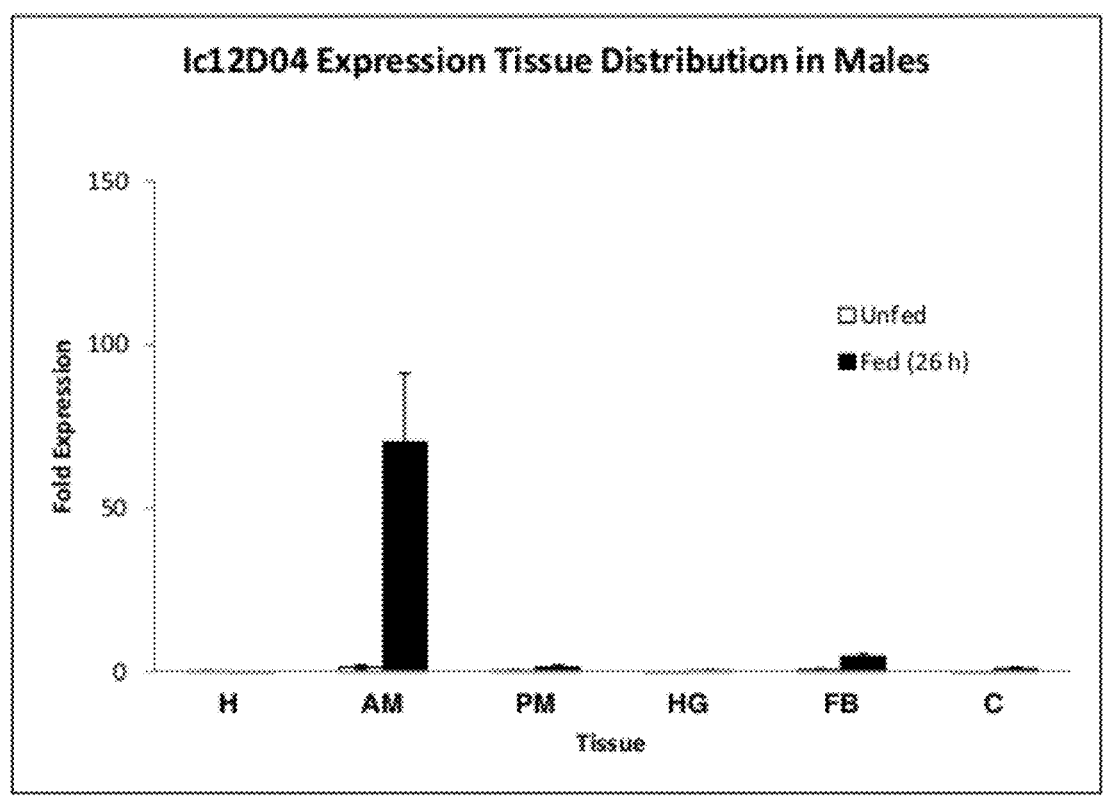
FIG. 7 is graphs of qRT-PCR data illustrating differences in Ipi12D04 mRNA levels in various tissues of male (left graph) and female (right graph) *I. confusus* beetles.
Figure 7B:
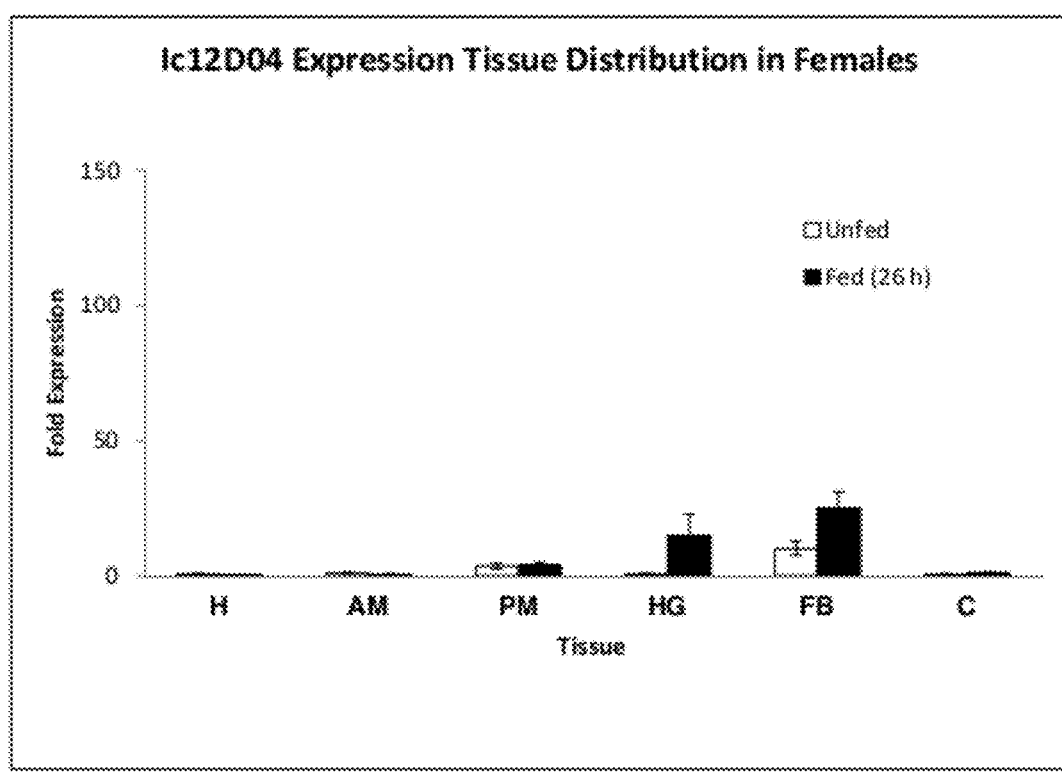

FIG. 5 illustrates qRT-PCR data of differentially expressed basal mRNA levels between male and female *I. pini* after JH III treatment (conditions that simulate pheromone production in male *I. pini*). Three mRNA showed particular enhancement. One of the identified mRNAs, Ipi12D04, was found to be localized predominantly to midgut tissue, more abundant in male midguts than female midguts, and to increase upon feeding and or topical treatment with JH III. Supporting Real-Time quantitative reverse-transcriptase PCR (qRT-PCR) data are shown in FIGS. 6 and 7.

Figure 8:
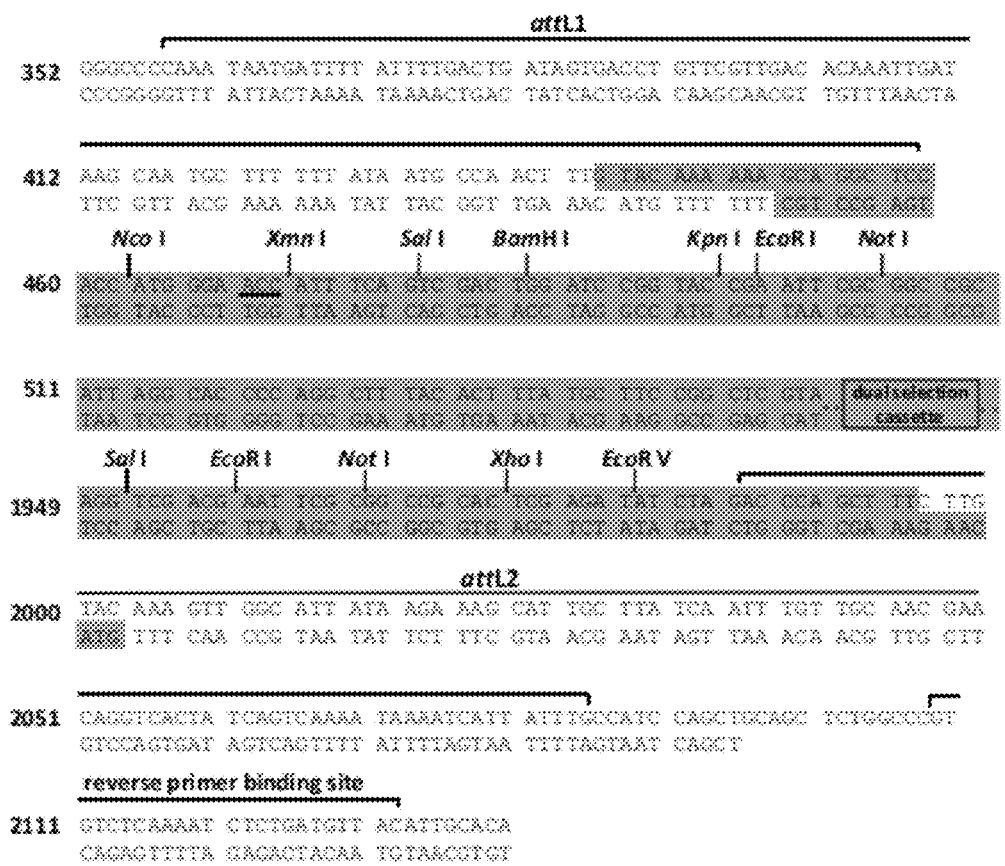
FIG. 8 is a sequence listing of a multiple cloning site portion of a vector (SEQ ID NOs: 6 and 7) used to produce transgenic cells according to an embodiment of the present disclosure.

Ipi12D04 function was determined by assays of recombinant protein expressed in a baculoviral system using Sf9 cells. The *Ips pini* 12D04 ORF was amplified from the expressed sequencing tag (EST) clone, 12D04 in pDONR222 by PCR with forward and reverse primers, 12D04F3 and 12D04R5 (Table 1). The amplification product was cloned into the EcoRI site of pENTR4 (Invitrogen) (modified to remove the NcoI site in the poly-linker (Sandstrom et al., Functional expression of a bark beetle cytochrome P450 that hydroxylates myrcene to ipsdienol. Insect Biochem Mol Biol. 36, 835-45 (2006)) (FIG. 8) by standard methods (Sambrook et al., Molecular Cloning, a Laboratory Manual. Cold Spring Harbor Laboratory Press, Cold Spring Harbor, Mass. (1989)) and transformed into DH5α cells. Screening for a correct orientation construct was done by PCR amplification and sequencing.

TABLE 1

| Cloning Primers | Sequence | Amplicon Length (bp) |
| --- | --- | --- |
| 12D04F3 | gcGAATTCtataaaaatcagttgacc (SEQ ID NO: 3) | 799 |
| 12D04R5 | gcGAATTCttaaggtctgagagcgc (SEQ ID NO: 4) | |

Invitrogen has detailed protocols for the growth and maintenance of Sf9 cells, recombinant baculovirus construction, and heterologous expression using the BaculoDirect™ Expression Kit. Briefly, an LR recombination reaction transferred the 12D04 ORF from the pENTR4 construct into the BaculoDirect™ Linear DNA and created the recombinant baculoviral 12D04 clone. This construct was transfected into Sf9 cells and grown in the presence of ganciclovir for negative selection against non-recombinant virus. High titer P3 viral stocks were created by successive 72 hour amplifications of the initial (P1) and P2 viral stocks. Plaque assays were performed on the P2 and P3 virus stocks to establish the viral titters. A P3 viral stock multiplicity of infection (MOI, pfu/cell) of 8 was used to infect Sf9 cells grown at a density of $1.0 \times 10^6$ cells/ml in a disposable 250 ml shaker flask.

Infected Sf9 cells were grown for 72 hours before the culture media, containing the recombinant 12D04 protein, was isolated. Briefly, cells were pelleted by centrifugation at 3000 g at 4° C. for 10 minutes. The supernatant was collected and cells were discarded.

Recombinant protein production was established by western blot using 1: 1,000 Anti-12D04 primary antibody (GenScript), 1:5,000 Goat Anti-Rabbit secondary antibody (Biorad, Hercules, Calif.) and SuperSignal West Pico Chemiluminescent Substrate (Pierce, Rockford, Ill.).

An affinity-purified polyclonal antibody (rabbit) for 12D4 was produced for our work by GenScript Corporations. The peptide sequence (see below) was designed from the *Ips pini* 12D04 amino acid sequence by Genscript with some modifications we suggested.

```
12D04 peptide sequence (14 amino acids long)
SRNEYKNEFPHDQC (SEQ ID NO: 5)
```

Enzyme activity is determined by a pyridine nucleotide (PN) binding assay that monitors production or consumption of NADH/NADPH by measuring the absorbance of the catalysts reaction at 340 nm using a spectrophotometer. The reactions include reaction buffer (0.1 M NaP pH 7.8 and 1.1 mM EDTA), enzyme, PN, and substrate (monoterpene) in a 1 ml total volume and the absorbance was measured over time at room temperature. The volatiles produced from the reactions were extracted three times with pentane:ether (1:1) spiked with 200 n g/ml n-octanol (internal standard) and concentrated to approximately 100 ul with nitrogen gas. The samples were directly analyzed by coupled GC-MS at the Nevada Proteomics Center at UNR.

Enzyme activity was determined by a pyridine nucleotide (PN) binding assay that monitored production or consumption of NADH/NADPH spectrophotometrically. The reaction mixture included reaction buffer (0.1 M NaP pH 7.8 and 1.1 mM EDTA), enzyme, PN, and substrate (monoterpene) in a 1 ml total volume. The absorbance was measured over time at room temperature. The reactions were extracted three times with pentane:ether (1:1) spiked with 200 ng/ml n-octanol (internal standard) to extract monoterpenoids and concentrated to approximately 100 ul with nitrogen gas. The samples were directly analyzed by coupled GC-MS at the Nevada Proteomics Center at UNR.

Biochemical reactions catalyzed by recombinant Ipi12D04, as determined by functional assays, are summarized below. In general, the enzyme functions as an oxidoreductase, using NAD(P) or NAD(P)H as cofactors, depending on whether it is oxidizing or reducing a substrate. Biochemical evidence (gas chromatographs, mass specta) supporting these activities is provided in FIGS. 9-21. In this data, recombinant Ipi12D04 was provided by the media of cells infected with recombinant baculovirus. Negative controls for all reactions included media from un-infected cells. All negative controls did not show metabolism of ipsdienol, ipsenol, or ipsdienone.

Figure 9:
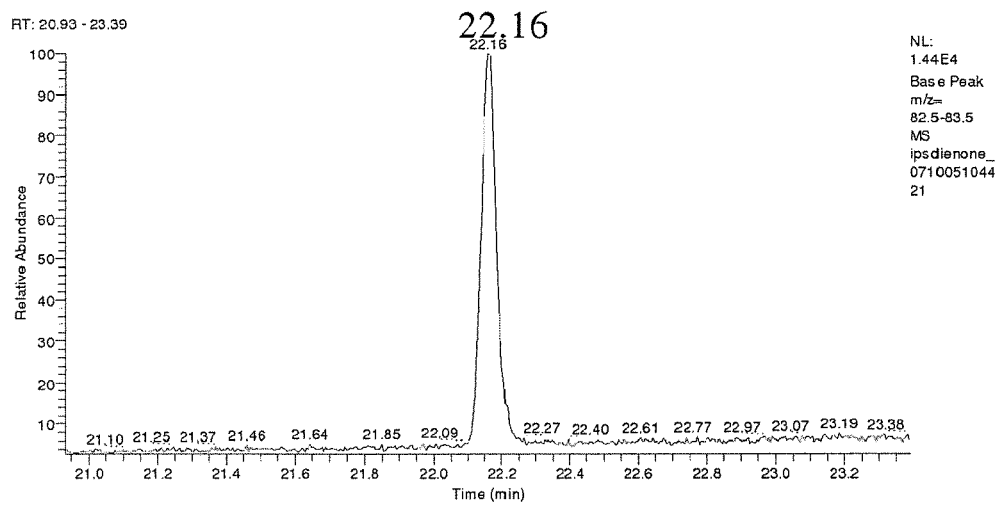
FIG. 9 is gas chromatogram of an ipsdienone standard.
Figure 10:
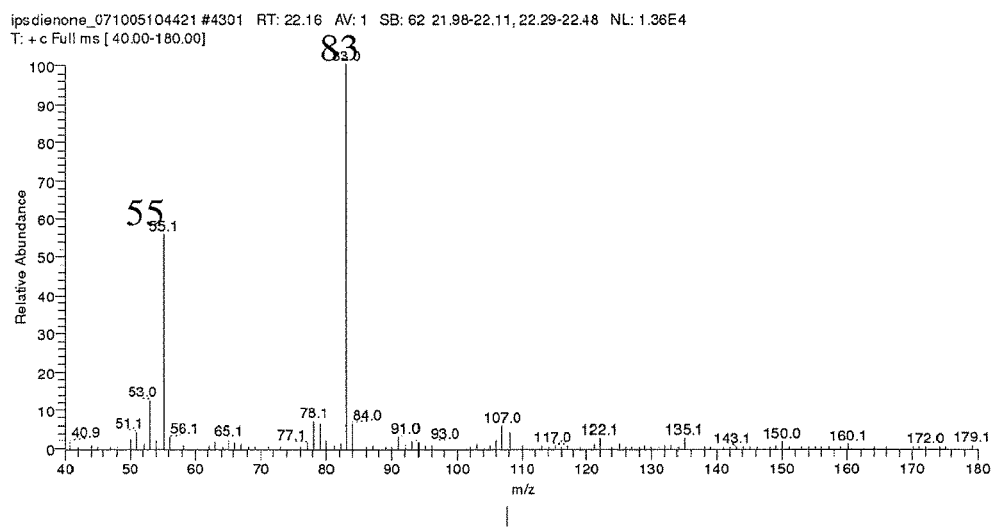
FIG. 10 is a mass spectrum of an ipsdienone standard.
Figure 11:
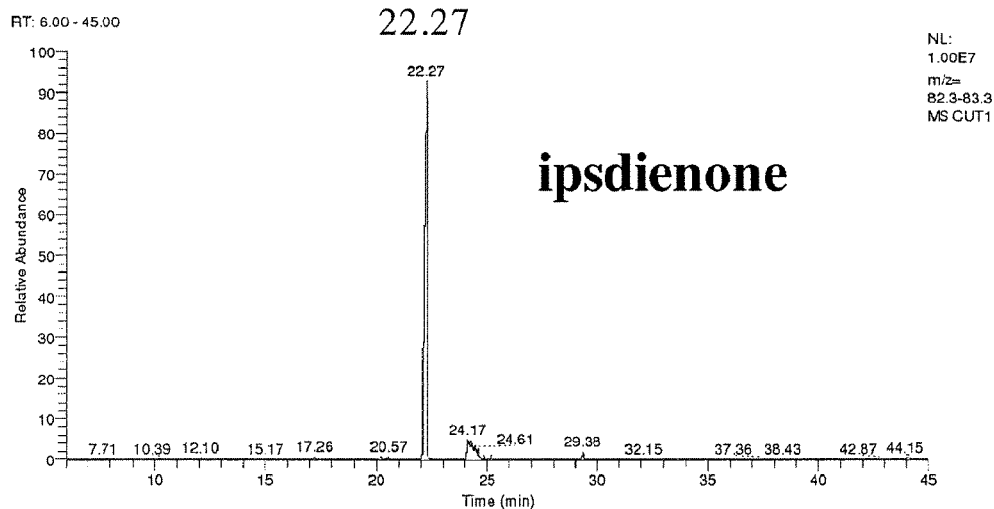
FIG. 11 is a gas chromatogram of ipsdienone produced by Ipi12D04 enzyme according to an embodiment of the present disclosure.
Figure 12:
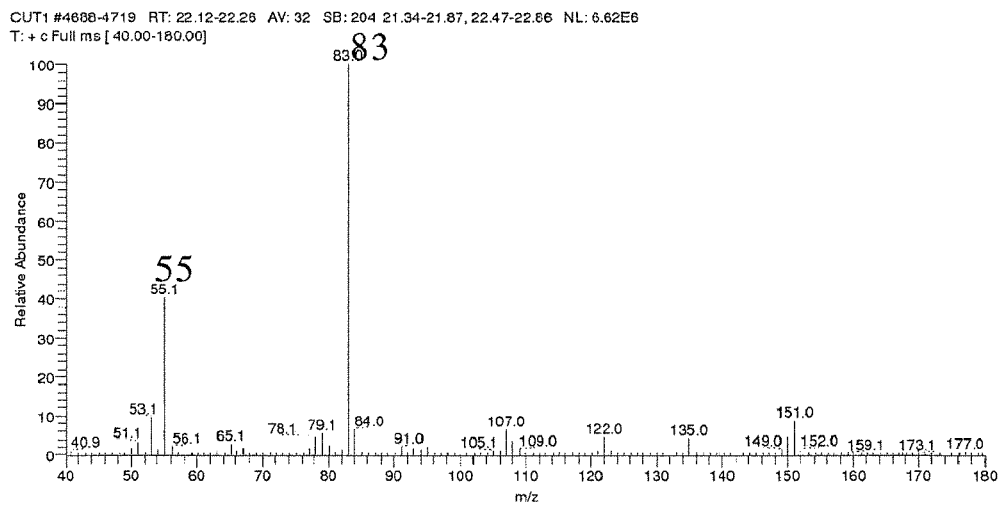
FIG. 12 is a mass spectrum of ipsdienone produced by Ipi12D04 enzyme according to an embodiment of the present disclosure.

FIG. 9 is a gas chromatogram of an ipsdienone standard while FIG. 10 is a corresponding mass spectrum. FIG. 11 is a gas chromatogram of ipsdienone produced using Ipi12D04 and NADP from racemic ipsdienol, FIG. 12 is a corresponding mass spectrum of this product. These results demonstrate that expressed Ipi12D04 enzymes converts racemic ipsdienol to ipsdienone.

Figure 13:
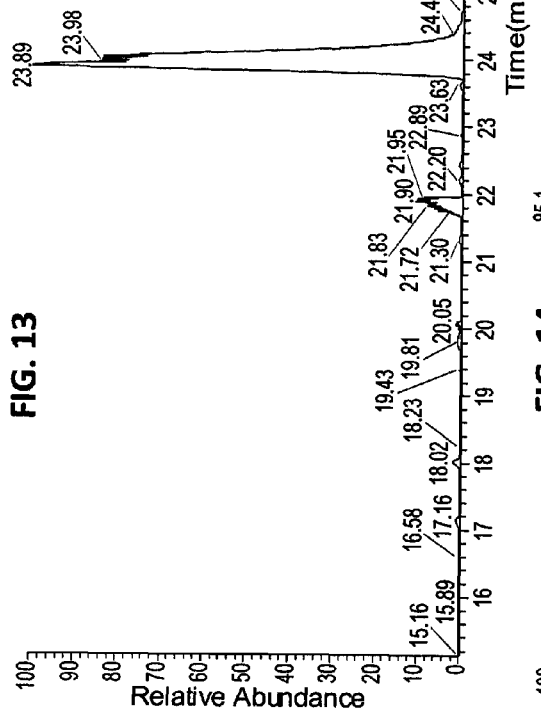
FIG. 13 is a gas chromatogram of the reaction product produced by the action of Ipi12D04 enzyme on ipsdienone.
Figure 14:
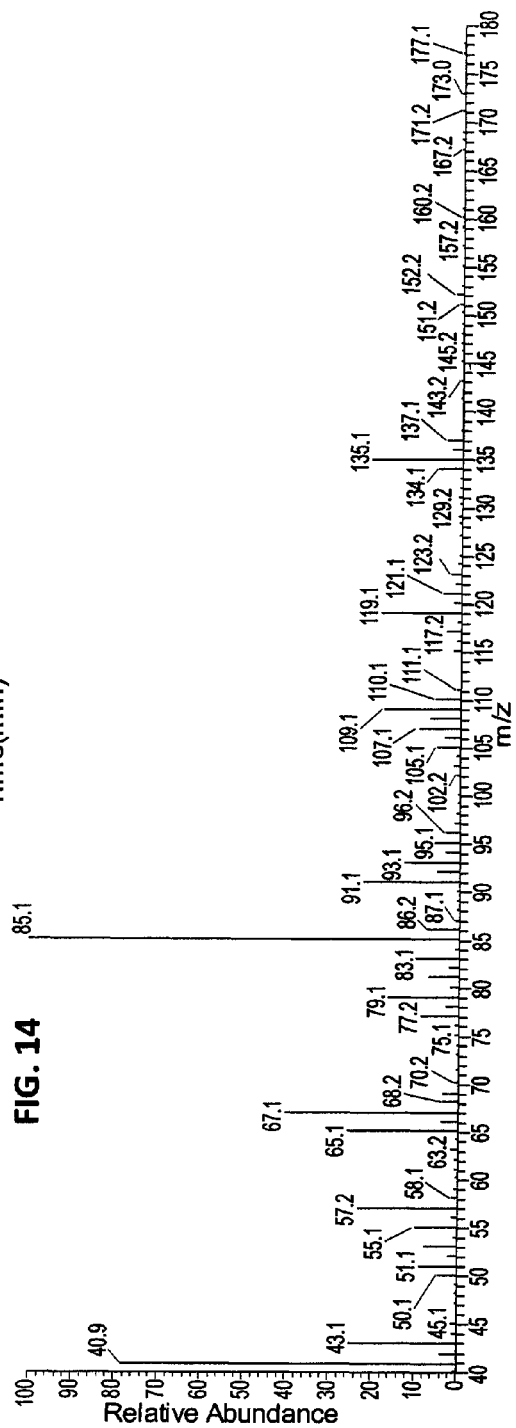
FIG. 14 is a mass spectrum of the reaction product produced by the action of Ipi12D04 enzyme on ipsdienone.
Figure 15:
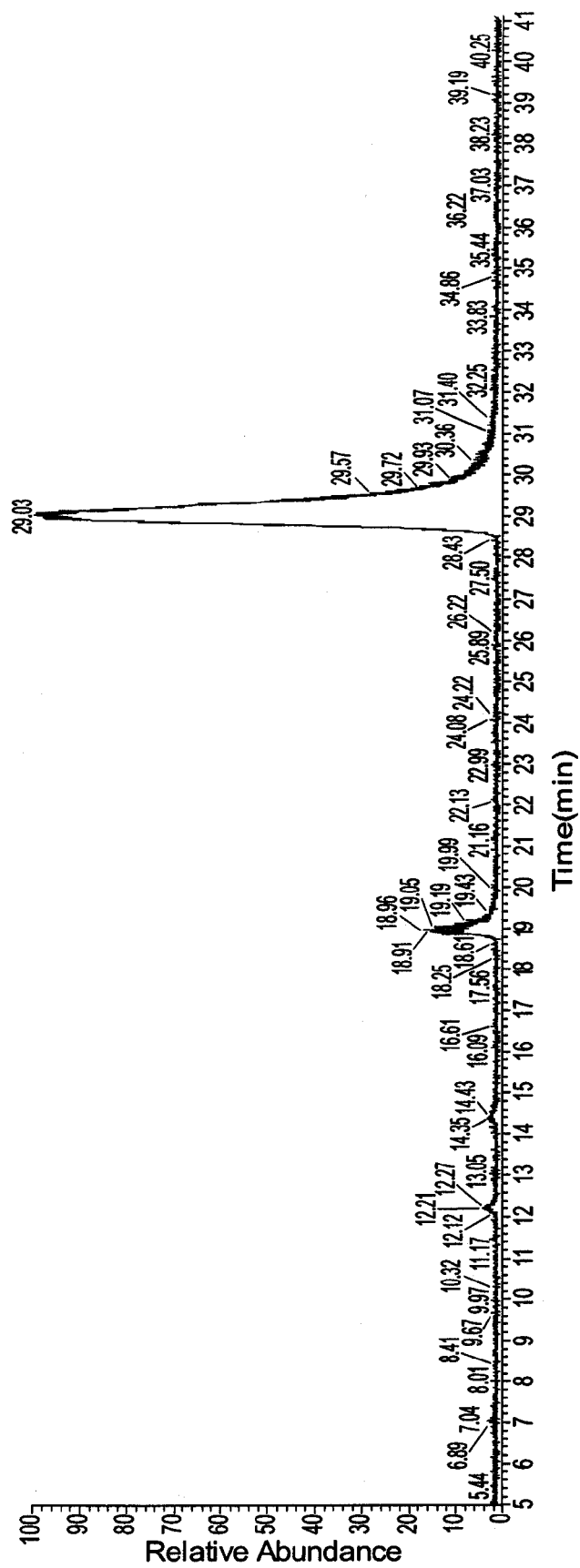
FIG. 15 is a gas chromatogram of the reaction product produced by the action of Ipi12D04 enzyme on ipsdienone, the column used being a chiral column.
Figure 16:
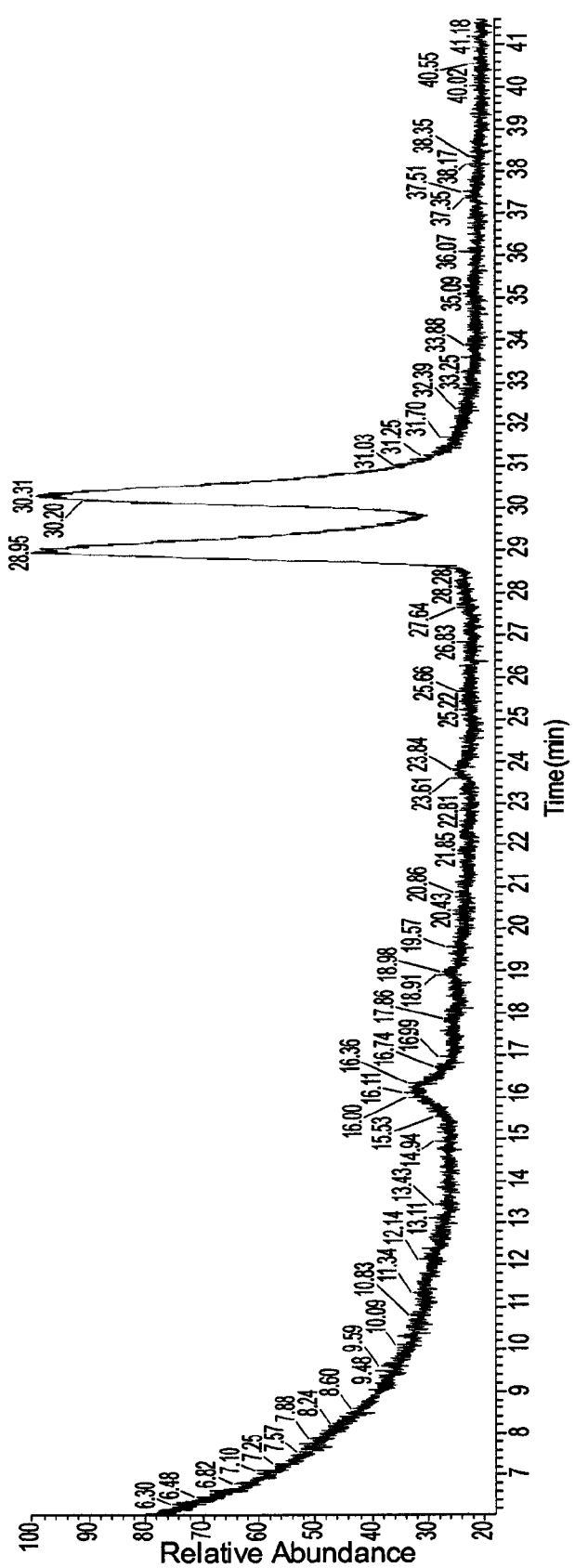
FIG. 16 is a gas chromatogram of a racemic ipsdienol standard on a chiral column.
Figure 17:
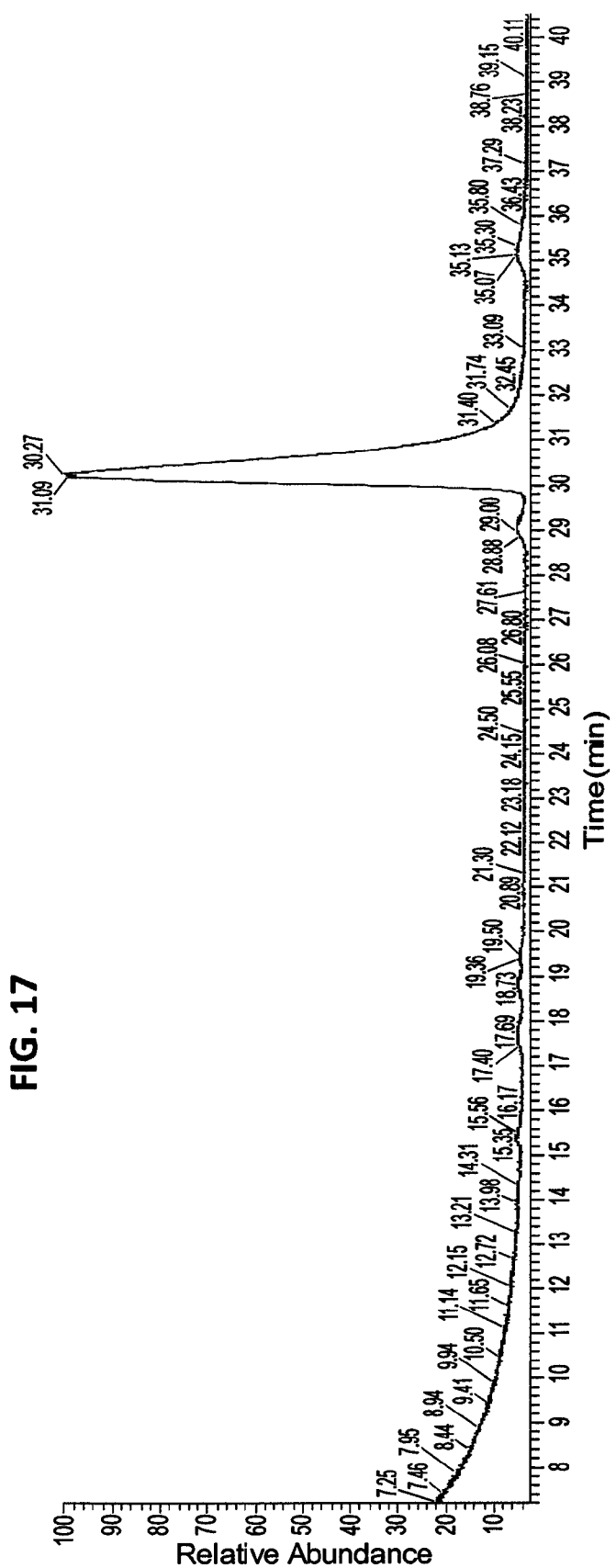
FIG. 17 is a gas chromatogram of an (+)-ipsdienol standard.
Figure 20:
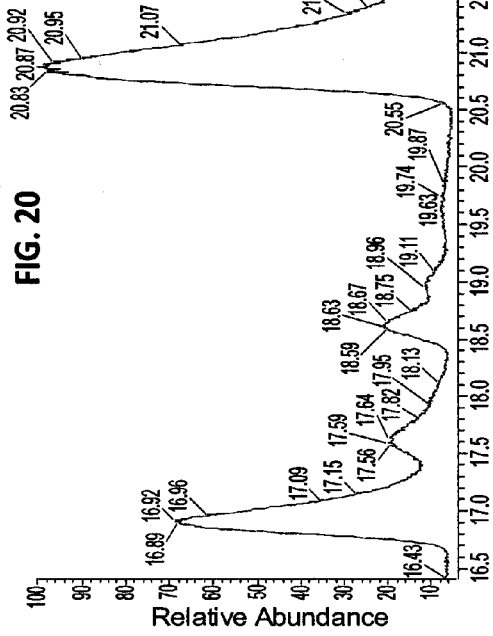
FIG. 20 is a gas chromatogram of the reaction product produced by the action of Ipi12D04 on ipsenone, the column used being a chiral column.
Figure 21:
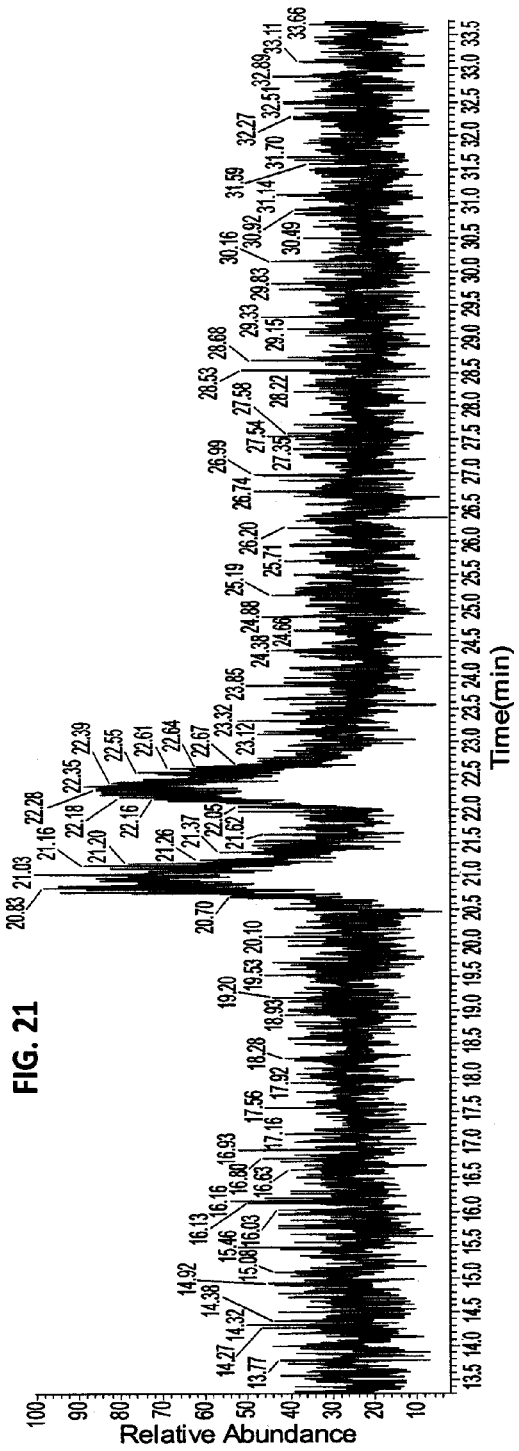
FIG. 21 is a gas chromatogram of a racemic ipsenol standard on a chiral column.

The action of Ipi12D04 enzyme on ipsdienone was also studied. FIG. 13 is a gas chromatogram of the reaction product, while FIG. 14 is a mass spectrum of the product. The gas chromatogram and mass spectrum are identical to an ipsdienol standard. In order to determine which stereoisomer was produced, the reaction product was separated on a chiral column, the gas chromatogram shown in FIG. 15. Comparison with gas chromatograms of racemic ipsdienol (FIG. 16) and pure (−)-ipsdienol standard (FIG. 17) confirmed that the reaction product was pure (−)-ipsdienol.

FIGS. 18 and 19 are, respectively, a gas chromatogram and a mass spectrum of the reaction product formed from the action of Ipi12D04 enzyme on ipsenone in the presence of NADPH. These data were identical to an ipsenol standard. In order to determine which stereoisomer was produced, the reaction product was separated on a chiral column, the gas chromatogram shown in FIG. 20. Comparison with the gas chromatogram of racemic ipsenol, FIG. 21, confirmed that the reaction product was pure (−)-ipsdienol.

It is expected that Ipi12D04 enzyme will convert any mixture of ipsdienol enantiomers into (−)-ipsdienol if the enzyme is incubated with both NAD(P) and NAD(P)H. The oxidation step may be stereo-selective for (+)-ipsdienol as a substrate. Similarly, (+)-ipsenol should be readily converted to (−)-ipsenol in a similar manner.

It is to be understood that the above discussion provides a detailed description of various embodiments. The above descriptions will enable those of ordinary skill in the art to make and use the disclosed embodiments, and to make departures from the particular examples described above to provide embodiments of the methods and apparatuses constructed in accordance with the present disclosure. The embodiments are illustrative, and not intended to limit the scope of the present disclosure. The scope of the present disclosure is rather to be determined by the scope of the claims as issued and equivalents thereto.

The invention claimed is:

1. An isolated, synthetic, or recombinant polynucleotide sequence at least 95% homologous to the sequence of SEQ ID NO:1 which encodes a polypeptide having oxidation reduction or oxidoreductase activity.

2. The polynucleotide sequence of claim 1, wherein the sequence is at least 99% homologous to the sequence of SEQ ID NO:1.

3. A fragment of the polynucleotide sequence of claim 1, that encodes a polypeptide having oxidation reduction or oxidoreductase activity.

4. A method of producing a polypeptide having oxidation or reduction activity comprising:
   introducing the polynucleotide of claim 1 into an isolated host cell;
   culturing the host cell;
   expressing from the host cell a polypeptide, wherein the polypeptide has oxidation or reduction activity; and
   isolating the polypeptide.

5. A method of generating a variant of a polypeptide having oxidation or reduction activity comprising:

providing a template nucleic acid comprising a sequence encoding a polypeptide at least 95% amino acid sequence similarity to the polypeptide encoded by the sequence of SEQ ID NO:1;
modifying, deleting or adding one or more nucleotides in the template sequence, or a combination thereof, to generate a variant of the template nucleic acid, wherein the variant encodes a polypeptide having oxidation or reduction activity; and
determining whether the polypeptide encoded by the variant catalytically oxidizes or reduces a substrate.

6. The method of claim 5, wherein the substrate comprises one or more of ipsenone, ipsenol, ipsdienone, and ipsdienol.

7. A transgenic host cell produced by inserting the polynucleotide of claim 1 into the host cell.

8. An isolated transgenic host cell produced by inserting a polynucleotide of claim 1.

9. The isolated, synthetic, or recombinant polynucleotide sequence of claim 1, wherein the polynucleotide sequence is the sequence of SEQ ID NO:1.

* * * * *